United States Patent [19]

Yamasaki et al.

[11] Patent Number: 5,576,331
[45] Date of Patent: Nov. 19, 1996

[54] AGENT FOR PREVENTING AND TREATING DISTURBANCES OF INTESTINAL MUCOUS MEMBRANE

[75] Inventors: Katsuya Yamasaki; Kazushi Sakurai; Kazue Akiyama; Toshihiro Osaka, all of Tokushima, Japan

[73] Assignee: Otsuka Pharmaceutical Co., Ltd., Tokyo, Japan

[21] Appl. No.: 256,372

[22] PCT Filed: Nov. 19, 1993

[86] PCT No.: PCT/JP93/01700

§ 371 Date: Jul. 22, 1994

§ 102(e) Date: Jul. 22, 1994

[87] PCT Pub. No.: WO94/12182

PCT Pub. Date: Jun. 9, 1994

[30] Foreign Application Priority Data

Nov. 26, 1992 [JP] Japan .................... 4-316852
Sep. 17, 1993 [JP] Japan .................... 5-231353

[51] Int. Cl.⁶ .................... A61K 31/47
[52] U.S. Cl. .................... 514/312
[58] Field of Search .................... 514/312

[56] References Cited

U.S. PATENT DOCUMENTS 4,578,381  3/1986  Uchida et al. .................... 514/233

FOREIGN PATENT DOCUMENTS

3324034A1  1/1984  Germany .
63-35623   7/1988  Japan .
3-74329    3/1991  Japan .
3-145468   6/1991  Japan .

OTHER PUBLICATIONS

"Sucralfate Treatment of Nonsteroidal Anti-Inflammatory Drug-Induced Gastrointestinal Symptoms and Mucosal Damage", Caldwell et al., The American Journal of Medicine, vol. 83 (suppl. 3B), pp. 74–82, Sep. 28, 1987.

"Prevention of gastroduodenal damage induced by non-steroidal anti-inflammatory drugs: controlled trial of ranitidine", Ehsanullah et al., British Medical Journal, vol. 297, pp. 1017–1021, Oct. 22, 1988.

"Effect of OPC–12759, a Novel Antiulcer Agent, on Chronic and Acute Experimental Gastric Ulcer, and Gastric Secretion in Rats", Yamasaki et al., Japan J. Pharmacol., vol. 49, No. 4, pp. 441–448, 1989.

"Protective effect of rebamipide (OPC–12759) on the gastric mucosa in rats and humans", Kawano et al., *Folia pharmacol. japon.*, vol. 97, No. 6, pp. 371–380, 1991.

"Effect of Rebamipide on Mucus Secretion by Endogenous Prostaglandin–independent Mechanism in Rat Gastric Mucosa", Ishihara et al., Arzneim.–Forsch./Drug Res., vol. 42, No. 12, pp. 1462–1466, 1992.

*Primary Examiner*—Samuel Barts
*Attorney, Agent, or Firm*—Finnegan, Henderson, Farabow, Garrett & Dunner

[57] ABSTRACT

A method for preventing and treating disturbances of intestinal mucous membrane comprising administering to a patient in need thereof an effective amount of the compound 2-(4-chlorobenzoylamino)-3-(2-quinolon-4-yl) propionic acid or a pharmaceutically acceptable salt thereof.

9 Claims, No Drawings

AGENT FOR PREVENTING AND TREATING DISTURBANCES OF INTESTINAL MUCOUS MEMBRANE

This application was filed under 35 U.S.C. 371 from the application PCT/JP93/01700 filed Nov. 19, 1993.

BACKGROUND OF THE INVENTION

The present invention relates to an agent for preventing and treating disturbances of intestinal mucous membrane. More particularly, the present invention relates to an agent for preventing and treating disturbances of intestinal mucous membrane, comprising, as the active ingredient, a carbostyril derivative represented by the following general formula (I):

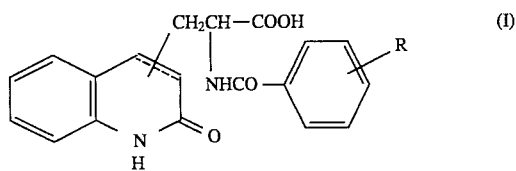

(wherein, R is a halogen-atom (a fluorine atom, a chlorine atom, a bromine atom or an iodine atom); the substituent on the carbostyril skeleton is at the 3- or 4-position of the carbostyril skeleton; and the bond between the 3- and 4-positions of the carbostyril skeleton is a single bond or a double bond) or a salt thereof, preferably 2-(4-chlorobenzoylamino)-3-(2-quinolon-4-yl)propionic acid or a salt thereof.

[Prior Art and Problems to Be Solved by the Invention]

The carbostyril derivatives represented by the above general formula (I) and the processes for production of said derivatives are described in Japanese Patent Publication No. 63-35623, etc. and the utility of said derivatives as an inhibitor for gastric ulcer is known. Further, the utility of the derivatives as a gastritis-treating agent is described in Japanese Patent Application Kokai (Laid-Open) No. 3-74329, and the processes for producing those compounds of said derivatives having an optical activity are described in Japanese Patent Application Kokai (Laid-Open) No. 3-145468.

Furthermore, inhibiting effect of compounds of the present invention on reactive oxygen metabolites is described in Japan. J. Pharmacol., Vol. 49, pp. 441–448 (1989), and the gastric mucous membrane protectability of the present invention compounds is described in Folia pharmacol. japon., Vol. 97, pp. 371–380 (1991).

Disturbances of intestinal mucous membrane include simple and primary ulcer of small intestine, nonspecific ulcer of colon, ulcerative colitis induced by nonspecific inflammations, Crohn's disease, etc., all of which appear owing to unknown causes. Disturbances of intestinal mucous membrane also appear owing to known causes such as infections, circular disturbances, collagen disease, radiations, medicines and the like. These disturbances of intestinal mucous membrane are generally hard to cure and, in some cases, surgical treatments are applied thereto. As the medicinal therapy for the disturbances, there are used adrenocortical steroids, Salazopyrin, immunosuppressive agents, etc. However, the steroidal drugs show side effects when administered in a large amount over a long period of time, and the immunosuppressive agents must be carefully used because of the very harmful side effects. Hence, it is desired to develop a medicine which is effective to the treatment of intractable disturbances of intestinal mucous membrane and which can be used safely over a long period of time.

Nonsteroidal anti-inflammatory drugs (hereinafter referred to as NSAID), which are widely used for various diseases attended by inflammations such as arthritis, chronic rheumatoid arthritis and the like, are known to give rise to disturbances of intestinal mucous membrane. The administration of these drugs must therefore be stopped in the middle in some cases. In patients of chronic rheumatoid arthritis, the treatment of rheumatism must be continued even when disturbances of intestinal mucous membrane have appeared, which requires the continued use of NSAID in such cases and poses a problem.

Under such a situation, various attempts were made to administer NSAID without incurring any disturbance of intestinal mucous membrane. For example, it was attempted to use a drug such as Sucralfate, Ranitidine (a histamine $H_2$ blocker) or the like in combination with NSAID [e.g. Caldwell, J. R., et al., Am. J. Med., Vol. 83, pp. 74–82, 1987, and Ehsanullah, R. S. B. et al., Br. Med. J., Vol. 297, pp. 1017–1021, 1988]. However, no satisfactory result has been obtained yet.

SUMMARY OF THE INVENTION

The present inventors made an extensive study in order to find out a novel drug useful for prevention and treatment of disturbances of intestinal mucous membrane. As a result, the present inventors found that the carbostyril derivatives represented by the above general formula (I) or salts thereof, in particular, 2-(4-chlorobenzoylamino)-3-(2-quinolon-4-yl)propionic acid or a salt thereof is useful for the prevention and treatment of disturbances of intestinal mucous membrane which are hard to cure. The finding has led to the completion of the present invention.

DETAILED DESCRIPTION OF THE INVENTION

The present agent for preventing and treating disturbances of intestinal mucous membrane, when used by itself, is prepared in any form of ordinary pharmaceutical preparations each comprising a carbostyril derivative of general formula (I) or a salt thereof. Such preparations are prepared using diluents or excipients ordinarily employed, such as filler, extender, binder, wetting agent, disintegrating agent, surfactant, lubricant and the like. The pharmaceutical preparations can take various forms depending upon how they are administered for treatment, and typical examples of the forms are tablets, pills, a powder, a liquor, a suspension, an emulsion, granules, capsules, suppositories and injection preparations (solution, suspension, etc.).

For the purpose of shaping into the form of tablets, known carriers widely used in this field can be used. They are exemplified by excipients such as lactose, white sugar, sodium chloride, glucose, urea, starch, calcium carbonate, kaolin, crystalline cellulose, silicic acid and the like; binders such as water, ethanol, propanel, simple syrup, glucose solution, starch solution, gelatin solution, carboxymethyl cellulose, shellac, methyl cellulose, calcium phosphate, polyvinyl pyrrolidone and the like; disintegrating agents such as dried starch, sodium alginate, agar powder, laminalia powder, sodium hydrogencarbonate, calcium carbonate, polyoxyethylene sorbitan fatty acid ester, sodium lauryl sulfate, monoglyceride of stearic acid, starch, lactose and the like; disintegration inhibitors such as sucrose, stearin, coconut butter, hydrogenated oil and the like; absorption accelerators such as quaternary ammonium base, sodium lauryl sulfate and the like; wetting agents such as glycerine, starch and the like; adsorbing agents such as starch, lactose, kaolin, bentonite, colloidal silicic acid and the like; and lubricants such as purified talc, stearic acid salt, boric acid powder, polyethylene glycol and the like. If necessary, the tablets can further be coated with ordinary coating materials to make them into coated tablets such as sugar-coated tablets, gelatin-coated tablets, enteric-coated tablets, film-coated tablets, double-layer tablets, multiple-layer tablets and the like.

For the purpose of shaping into the form of pills, known carriers widely used in this field can be used. They are exemplified by excipients such as glucose, lactose, starch, coconut butter, hydrogenated vegetable oil, kaolin, talc and the like; binders such as powdered gum arabic, powdered tragacanth gum, gelatin, ethanol and the like; and disintegrating agents such as laminaria, agar and the like.

For the purpose of shaping into the form of suppositories, known carriers widely used in this field can be used. They are exemplified by polyethylene glycol, coconut butter, higher alcohols, higher alcohol esters, gelatin and semi-synthetic glycerides.

For the purpose of making into the form of injection preparations, solutions, emulsions or suspensions are prepared and are generally further sterilized and preferably made isotonic to the blood. In preparing the injection preparations in the form of solutions, emulsions or suspensions, any known carrier widely used in this field can be used. It is exemplified by water, ethanol, propylene glycol, ethoxylated isostearyl alcohol, polyoxylated isostearyl alcohol and polyoxyethylene sorbitan fatty acid esters. The solutions, emulsions or suspensions may further contain sodium chloride, glucose or glycerine in an amount sufficient to make them isotonic to the blood. The solutions, emulsions or suspensions may furthermore contain a dissolving agent, a buffer solution, an analgesic agent, etc. all of ordinary use and, as necessary, a coloring agent, a preservative, a perfume, a seasoning agent, a sweetening agent and other medicines.

When the administration of NSAID must be continued for the treatment of diseases such as rheumatism and the like and therefore the present agent for preventing and treating disturbances of intestinal mucous membrane is used in combination with NSAID, it is preferable to administer the two medicines simultaneously. The two medicines may be administered as different medicines or as a mixed agent containing the two medicines.

The NSAID's with which the present agent is used in combination, are not particularly restricted and include all NSAID's widely used, such as Aspirin, Indomethacin, Diclofenac, Ibuprofen, Naproxen, Piroxicam, Mefenamic Acid, Flufenamic Acid, Floctafenine, Ethenzamide, Sodium salicylate, Diflunisal, Clofezone, Ketophenylbutazone, Phenylbutazone, Alclofenac, Alminoprofen, Ketoprofen, Flurbiprofen, Pranoprofen, Loxoprofen-Na, Tiaramide hydrochloride, Perisoxal citrate, Emorfazone, Acemetacin, Proglumetacin maleate, Bucolome and the like.

The amount of the present agent administered is appropriately determined depending upon the administration method, the age, sex and other conditions of patient, the degree of disease, etc. However, the preferable amount is generally 0.6–50 mg per kg of body weight per day in terms of the amount of carbostyril derivative of general formula (I) or salt thereof. The preferable amount of active ingredient in each application unit form is 10–1,000 mg when used in combination with NSAID. The present agent, when used in combination with NSAID, is used in an amount of generally 0.1–100 parts by weight per 1 part by weight of NSAID although the amount differs depending upon the kind of the NSAID used in combination. Therefore, when the present agent is used as a mixed agent containing both the present agent and NSAID, the desirable weight ratio of the present agent and NSAID is 0.01–10, preferably 0.1–10. That is, in the mixed agent containing both the present agent and NSAID, each administration unit form generally contains 10–1,000 mg of a carbostyril derivative of general formula (I) or a salt thereof and 1–1,000 mg of NSAID.

The amount of the carbostyril derivative of general formula (I) or the salt thereof contained in the present agent for preventing and treating disturbances of intestinal mucous membrane is not particularly restricted and can be selected from a wide range. However, the amount is generally 10–70% by weight, preferably, 10–50% by weight based on the total composition. When the present agent is used as a mixed agent containing both the present agent and NSAID, the total amount of the carbostyril derivative (I) or the salt thereof and NSAID is 10–90% by weight, preferably 30–70% by weight based on the total composition.

The present agent for preventing and treating disturbances of intestinal mucous membrane is useful for intractable disturbances of intestinal mucous membrane, particularly, ulcerative colitis and drug-induced disturbances of intestinal mucous membrane.

Next, the present agent for preventing and treating disturbances of intestinal mucous membrane is described specifically by showing examples of pharmaceutical preparations as well as pharmacological tests.

| Pharmaceutical Preparation 1 | |
|---|---|
| 2-(4-Chlorobenzoylamino)-3-(2-quinolon-4-yl)propionic acid | 150 g |
| Avicel (a trademark for microcrystalline cellulose manufactured by Asahi Chemical Industry Co., Ltd.) | 40 g |
| Corn starch | 30 g |
| Magnesium stearate | 2 g |
| Hydroxypropylmethyl cellulose | 10 g |
| Polyethylene glycol 6000 | 3 g |
| Castor oil | 40 g |
| Methanol | 40 g |

The compound of the present invention [2-(4-chlorobenzoylamino)-3-(2-quinolon-4-yl)propionic acid], Avicel, corn starch and magnesium stearate are mixed and ground. The mixture is shaped into tablets by using a punch having a diameter of 10 mm. The tablets are coated with a film coating agent consisting of hydroxypropylmethyl cellulose, polyethylene glycol 6000, castor oil and methanol to prepare film-coated tablets.

| Pharmaceutical Preparation 2 | |
|---|---|
| 2-(4-Chlorobenzoylamino)-3-(2-quinolon-4-yl)propionic acid | 150 g |
| Citric acid | 1.0 g |
| Lactose | 33.5 g |
| Calcium secondary phosphate | 70.0 g |
| Pluronic F-68 (a trademark for a nonionic polyoxyalkylene derivative of propylene glycol manufactured by BASF-Wyandotte Corp.) | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |

| Pharmaceutical Preparation 2 | |
|---|---|
| Corn starch | 30.0 g |
| Dried sodium lauryl sulfate | 3.0 g |
| Dried magnesium stearate | 3.0 g |
| Ethanol | Necessary amount |

The compound of the present invention [2-(4-chlorobenzoylamino)-3-(2-quinolon-4-yl)propionic acid], citric acid, lactose, calcium secondary phosphate, Pluronic F-68 and sodium lauryl sulfate are mixed.

The mixture is sieved through a No. 60 screen and then made into wet granules by using an alcholic solution containing polyvinylpyrrolidone, Carbowax 1500 and Carbowax 6000. As necessary, ethanol is added to make the granules into a paste-like semi-solid. Corn starch is added thereto and the mixture is kneaded until granules of uniform size are formed. The granules are passed through a No. 10 screen, placed in a tray, and dried in an oven of 100° C. for 12–14 hours. The dried granules are sieved through a No. 16 screen. The granules which have passed through the screen, are mixed with dried sodium lauryl sulfate and dried magnesium stearate. The mixture is compressed into a desired shape by using a tablet machine.

The thus obtained tablets (each of which is to become the core portion of each multi-layer tablet obtained finally) are treated with a varnish at the surfaces. The varnish-treated surfaces are coated with talc so as to protect the surfaces from moisture absorption. Thereon is applied undercoating. Varnish coating is conducted sufficient times for oral administration. Undercoating and smooth coating are further applied to make the tablets completely spherical and smooth. Color coating is applied until a desired color is obtained. The resulting coated tablets are dried and then their surfaces are polished to obtain multi-layer tablets of uniform gloss.

| Pharmaceutical Preparation 3 | |
|---|---|
| 2-(4-Chlorobenzoylamino)-3-(2-quinolon-4-yl)propionic acid | 150 g |
| Aspirin | 150 g |
| Avicel | 40 g |
| Corn starch | 30 g |
| Magnesium stearate | 2 g |
| Hydroxypropylmethyl cellulose | 10 g |
| Polyethylene glycol 6000 | 3 g |
| Castor oil | 40 g |
| Methanol | 40 g |

The above materials each of indicated amount are made into film-coated tablets by the same procedure as in Pharmaceutical Preparation 1.

| Pharmaceutical Preparation 4 | |
|---|---|
| 2-(4-Chlorobenzoylamino)-3-(2-quinolon-4-yl)propionic acid | 150 g |
| Ibuprofen | 50.0 g |
| Citric acid | 1.0 g |
| Lactose | 33.5 g |
| Calcium secondary phosphate | 70.0 g |
| Pluronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |

| Pharmaceutical Preparation 4 | |
|---|---|
| Corn starch | 30.0 g |
| Dried sodium lauryl sulfate | 3.0 g |
| Dried magnesium stearate | 3.0 g |
| Ethanol | Necessary amount |

The above materials each of indicated amount are made into tablets by the same procedure as in Pharmaceutical Preparation 2.

Pharmacological Test 1

Inhibitory effect on acetic acid-induced ulcerative colitis 2-(4-Chlorobenzoylamino)-3-(2-quinolon-4-yl)-propionic acid was used as a test compound, and its inhibitory effect on acetic acid-induced ulcerative colitis was examined.

Test method:

Male Wistar or Wistar/ST rats (10 week-old and weighing between 250 g and 300 g), which had been fasted for 24 hours, were subjected to laparotomy under anesthesia with ether. The cecum of each rat was taken out to the body surface; the lower portion of the cecum (i.e. the cecum portion connecting to the colon) was once ligated; and 2 ml of 5% acetic acid was injected into the large intestine at the portion just below the ligated cecum portion, via a 27G injection needle. Immediately after the acetic acid injection, 3 ml of air was injected to discharge acetic acid from the anus. Then, the ligation was released and the abdomen was sutured. After this operation, each rat was fed as usual. 24 hours after operation, each rat was killed and the large intestine was extracted. The large intestine was cut longitudinally, opened and washed with a physiological saline solution to remove the contents, after which the washed large intestine was extended in a flat state. The lesion appearing in the mucous membrane of large intestine was observed by the naked eye and rated according to the following rating scale.

To each rat of each test group, the above-mentioned test compound dissolved in a solvent (a 0.5% carboxymethylcellulose aqueous solution) was orally administered twice a day (right after the acetic acid injection and 8 hours thereafter). To each rat of a reference group, only the above solvent was orally administered at the same timings as for the test compound administered to each test group. To each rat of a control group, nothing was administered.

Scale for rating the lesion appearing in mucous membrane of large intestine

Grade 0: no lesion.

Grade 1: hyperemia only.

Grade 2: hyperemia, or linear ulcer attended by no hypertrophy of intestinal wall.

Grade 3: linear ulcer attended by inflammation.

Grade 4: ulcer attended by two or more inflammations.

Grade 5: ulcer attended by two or more large inflammations, or one large lesion of at least 1 cm in size extending in the longitudinal direction of large intestine.

Grades 6 to 10: when the size of ulcer attended by inflammation exceeds 2 cm in the longitudinal direction of colon, grade increases by one (for example, from 6 to 7) per each 1 cm increase of said size.

Test results:

The results of the above test are shown in Table 1. As is clear from Table 1, the reference group, to which the above-mentioned solvent had been administered, showed high disturbances of mucous membrane of large intestine, as compared with the control group to which nothing was administered. Two times a day of oral administration of 30 mg/kg of the test compound significantly reduced the degree of acetic acid-induced ulcerative colitis.

TABLE 1

Inhibitory effect on acetic acid-induced ulcerative colitis

| Group | Dose of test compound (mg/kg, p.o., b.i.d.) | Number of rats | Grade of lesion of mocous membrane of large intestine |
|---|---|---|---|
| Control group | — | 8 | 0.0 ± 0.0 |
| Reference group | — | 8 | 6.3 ± 0.6 ## |
| Test groups | | | |
| A | 7.5 | 8 | 5.3 ± 0.8 ## |
| B | 15 | 8 | 5.3 ± 0.9 ## |
| C | 30 | 8 | 2.6 ± 0.6 ** |

In Table 1, grade data are shown in the form of average value ± standard error. Test of significance was conducted by non-parametric Dunnett type multiple comparison.

## indicates significance over the control group at p<0.01, and ** indicates significance over the reference group at p<0.01.

Pharmacological Test 2

Inhibitory effect on NSAID-induced disturbances of intestinal mucous membrane

To each rat (male Wistar rat) of each test group were simultaneously administered orally an NSAID of an amount showing an analgesic effect [Aspirin (75 mg/kg), Ibuprofen (20 mg/kg), Naproxen (3 mg/kg) or Piroxicam (2 mg/kg)] and 30 mg/kg of a test compound [2-( 4-chlorobenzoylamino)-3-(2-quinolon-4-yl)-propionic acid]. They were administered twice a day for 1 week. Then, each rat was fasted for 24 hours and killed under anesthesia with ether, followed by extraction of alimentary canal from each rat. The alimentary canal was cut along the greater curvature and opened, and the surface of the mucous membrane was observed by the naked eye to rate the disturbances appearing thereon. To each rat of each control group was administered only a NSAID, and the same test as above was conducted. The results are shown in Table 2.

TABLE 2

| Test Groups | Degree of disturbances | | |
|---|---|---|---|
| | Duodenum | Jejunum | Ileum |
| Aspirin alone | 2.2 ± 1.0 | 0.4 ± 0.2 | 0.2 ± 0.2 |
| Aspirin + test compound | 0 ± 0 | 0 ± 0 | 0 ± 0 |
| Ibuprofen alone | 1.6 ± 0.9 | — | 0.4 ± 0.2 |
| Ibuprefen + test compound | 1.2 ± 0.7 | — | 0 ± 0 |
| Naproxen alone | — | 0.6 ± 0.2 | — |
| Naproxen + test compound | — | 0 ± 0 | — |
| Piroxicum alone | — | 0.4 ± 0.4 | 0.6 ± 0.2 |
| Piroxicum + test compound | — | 0.2 ± 0.2 | 0 ± 0 |

The degrees of disturbances shown in Table 2 were rated using the following rating scale (grades 0 to (5) in accordance with the standard for rating of lesions of gastric mucosa by Adami et al. (Adami, E., et al.; Arch. int. Pharmacodyn. Ther., Vol. 147, Nos. 1–2, pp. 113–145, 1964).

Grade 0: no lesion.
Grade 1: hemorrhagic suffusion.
Grade 3: 5 or more small ulcers or one large ulcer.
Grade 4: many ulcers of marked size.
Grade 5: perforated ulcer.

As is clear from Table 2, all of the disturbances of mucous membranes of duodenum, jejunum and ileum, induced by NSAID were significantly reduced by the use of the present agent for preventing and treating intestinal mucous membrane, in combination with NSAID.

I claim:

1. A method for preventing and treating disturbances of intestinal mucous membrane comprising administering to a patient in need thereof a pharmaceutical composition comprising, as the active ingredient, an effective amount for preventing and treating disturbances of intestinal mucous membrane of 2-(4-chlorobenzoylamino)-3-(2-quinolon-4-yl) propionic acid or a pharmaceutically acceptable salt thereof and a pharmaceutically acceptable carrier.

2. A method for preventing inflammatory disturbances of intestinal mucous membrane comprising administering to a patient in need thereof a pharmaceutical composition comprising, as the active ingredient, an effective amount for preventing inflammatory disturbances of intestinal mucous membrane of 2-(4-chlorobenzoylamino)-3-(2-quinolon-4-yl) propionic acid or a pharmaceutically acceptable salt thereof and a pharmaceutically acceptable carrier.

3. A method for preventing drug-induced disturbances of intestinal mucous membrane comprising administering to a patient in need thereof a pharmaceutical composition comprising, as the active ingredient, an effective amount for preventing drug-induced disturbances of intestinal mucous membrane of 2-(4-chlorobenzoylamino)-3-(2-quinolon-4-yl) propionic acid or a pharmaceutically acceptable salt thereof and a pharmaceutically acceptable carrier.

4. A method for preventing nonsteroidal anti-inflammatory drug-induced disturbances of intestinal mucous membrane comprising administering to a patient in need thereof a pharmaceutical composition comprising, as the active ingredient, an effective amount for preventing nonsteroidal anti-inflammatory drug-induced disturbances of intestinal mucous membrane of 2-(4-chlorobenzoylamino)-3-(2-quinolon-4-yl) propionic acid or a pharmaceutically acceptable salt thereof and a pharmaceutically acceptable carrier.

5. A method for preventing and treating ulcerative colitis comprising administering to a patient in need thereof a pharmaceutical composition comprising, as the active ingredient, an effective amount for preventing and treating ulcerative colitis of 2-(4-chlorobenzoylamino)-3-(2-quinolon-4-yl) propionic acid or a pharmaceutically acceptable salt thereof and a pharmaceutically acceptable carrier.

6. The method of claim 1, wherein the intestinal mucous membrane is jejunum or ileum mucous membrane and the amount of the active ingredient administered is an effective amount for preventing and treating disturbances of jejunum or ileum mucous membrane.

7. The method of claim 2, wherein the intestinal mucous membrane is jejunum or ileum mucous membrane and the amount of the active ingredient administered is an effective amount for preventing inflammatory disturbances of jejunum or ileum mucous membrane.

8. The method of claim 3, wherein the intestinal mucous membrane is jejunum or ileum mucous membrane and the amount of the active ingredient administered is an effective amount for preventing drug-induced disturbances of jejunum or ileum mucous membrane.

9. The method of claim 4, wherein the intestinal mucous membrane is jejunum or ileum mucous membrane and the amount of the active ingredient administered is an effective amount for preventing non-steroidal anti-inflammatory drug-induced disturbances of jejunum or ileum mucous membrane.

* * * * *